United States Patent [19]

Huber et al.

[11] 4,022,877

[45] May 10, 1977

[54] RADIOACTIVE LABELED ORGOTEIN

[75] Inventors: Wolfgang Huber, Atherton; Mark G. Saifer, Berkeley; Lewis D. Williams, Menlo Park, all of Calif.

[73] Assignee: Diagnostic Data, Inc., Mountain View, Calif.

[22] Filed: Sept. 9, 1975

[21] Appl. No.: 611,656

[52] U.S. Cl. .............................. 424/1; 260/112 R; 424/9
[51] Int. Cl.² .................. A61K 29/00; A61K 43/00
[58] Field of Search .................. 424/1, 1.5, 9, 177; 260/112 R, 112 B

[56] References Cited

UNITED STATES PATENTS

| | | | |
|---|---|---|---|
| 3,637,640 | 1/1972 | Huber | 260/112 R X |
| 3,758,682 | 9/1973 | Huber et al. | 260/112 R X |
| 3,781,414 | 12/1973 | Huber | 424/12 |

OTHER PUBLICATIONS

Huber et al., Chemical Abstracts, vol. 76, No. 25, June 19, 1972, p. 69., Abstract No. 149230b Primary Examiner—Benjamin R. Padgett
Assistant Examiner—Christine M. Nucker
Attorney, Agent, or Firm—Millen & White

[57] ABSTRACT

Orgotein labeled with $^{99M}$Tc, or with a radioactive iodine isotope, preferably $^{131}$I, is useful in scintigraphy for tissue visualization, especially the kidneys.

10 Claims, No Drawings

RADIOACTIVE LABELED ORGOTEIN

BACKGROUND OF THE INVENTION

This invention relates to radioactive labeled orgotein.

Orgotein is the non-proprietary name assigned by the United States Adopted Name council to members of a family of water-soluble protein congeners in substantially pure, injectable form, i.e., substantially free from other proteins which are admixed or associated therewith in the sources thereof. U.S. Pat. No. 3,758,682 claims pharmaceutical compositions comprising orgotein. Various uses of orgotein are disclosed in U.S. Pat. Nos. 3,637,441; 3,773,928; 3,773,929; and 3,781,414.

The orgotein metalloproteins are members of a family of protein congeners having a characteristic combination of physical, chemical, biological and pharmacodynamic properties. Each of these congeners is characterized physically by being the isolated, substantially pure form of a globular, buffer and water-soluble protein having a highly compact native conformation which, although heat labile, is stable to heating for several minutes at 65° C. at pH 4–10. Chemically, each is characterized by containing all but 0–2 of the protein aminoacids, a small percentage of carbohydrate, no lipids, 0.1 to 1.0% metal content provided by one to 5 gram atoms per mole of one or more chelated divalent metals having an ionic radius of 0.60 to 1.00 A., and substantially no chelated monovalent metals or those that are cell poisons in the molecule. Table I lists the distribution of aminoacid residues, calculated for a molecular weight of 32,500 of several orgotein congeners.

TABLE I

AMINO ACID COMPOSITION OF SEVERAL ORGOTEIN CONGENERS
[Residues per mole, M.W. = 32,500]

| Aminoacids | Liver, Beef | Red Blood Cells (RBC) | | | | | | | | | Range |
| --- | --- | --- | --- | --- | --- | --- | --- | --- | --- | --- | --- |
| | | Beef | Sheep | Horse | Pork | Dog | Rabbit | Rat | Guinea Pig | Chicken | Human | |
| Alanine | 19 | 19 | 18 | 18 | 18 | 16 | 19 | 22 | 22 | 23 | 22 | 16–23 |
| Arginine | 8 | 8 | 10 | 6 | 8 | 8 | 8 | 7 | 8 | 8 | 8 | 6–10 |
| Aspartic acid | 37 | 36 | 35 | 35 | 31 | 29 | 34 | 30 | 34 | 36 | 37 | 29–37 |
| Cystine-1/2 | 6 | 6 | 6 | 6 | 6 | 6 | 6 | 6 | 4 | 10 | 8 | 4–10 |
| Glutamic acid | 21 | 23 | 22 | 30 | 28 | 30 | 25 | 38 | 29 | 26 | 28 | 21–38 |
| Glycine | 53 | 52 | 52 | 51 | 52 | 53 | 54 | 54 | 53 | 56 | 51 | 51–56 |
| Histidine | 16 | 16 | 14 | 20 | 16 | 15 | 17 | 20 | 15 | 17 | 14 | 14–20 |
| Isoleucine | 18 | 18 | 18 | 14 | 16 | 18 | 16 | 16 | 18 | 15 | 17 | 14–18 |
| Leucine | 17 | 17 | 17 | 18 | 16 | 16 | 19 | 12 | 17 | 15 | 20 | 12–20 |
| Lysine | 22 | 21 | 23 | 26 | 23 | 20 | 21 | 18 | 20 | 21 | 23 | 18–26 |
| Methionine | 2 | 2 | 2 | 2 | 2 | 6 | 3 | 4 | 2 | 3 | 1 | 1–6 |
| Phenylalanine | 8 | 8 | 7 | 9 | 8 | 8 | 9 | 6 | 8 | 8 | 8 | 6–9 |
| Proline | 12 | 13 | 15 | 10 | 10 | 10 | 13 | 10 | 12 | 13 | 12 | 10–15 |
| Serine | 17 | 17 | 14 | 14 | 13 | 20 | 18 | 18 | 18 | 15 | 19 | 13–30 |
| Threonine | 26 | 25 | 20 | 16 | 27 | 20 | 21 | 17 | 17 | 18 | 18 | 16–27 |
| Tryptophan[1] | Nil | Nil | Nil | Nil | Nil | Nil | Nil | Nil | Nil | 1 | 2 | 0–2 |
| Tyrosine[2] | 2 | 2 | 2 | Nil | 4 | 2 | Nil | 2 | Nil | 2 | Nil | 0–4 |
| Valine | 33 | 32 | 31 | 29 | 29 | 34 | 31 | 35 | 32 | 30 | 30 | 29–35 |
| Total | 317 | 315 | 306 | 304 | 307 | 311 | 315 | 315 | 309 | 317 | 318 | 304–318 |

[1]Colorimetric determination
[2]Average of amino acid analysis and spectrophotometric determination.

In 1969, the bovine congener of the orgotein protein was discovered to be an enzyme which has the ability to catalyze the destruction of superoxide radicals in a disproportionation into molecular oxygen and hydrogen peroxide. The name "superoxide dismutase" (SOD) was assigned to the protein on the basis of this enzymatic activity. McCord, J. M. and Fridovich, I., J. Biol. Chem. 244, 6049–6055 (1969).

Radioactive-labeled compounds are of great interest as diagnostic agents. Numerous radioactive diagnostic agents contain a radioactive halogen, especially iodine. For example, thyroxine-$I^{131}$ is used for thyroid diagnostics, sodium diatrizoate-$I^{131}$ for testing the kidney function, the sodium salt of tetrachlorotetraiodofluorescein-$I^{131}$ for testing liver function, bromthalein-$I^{131}$ for gall bladder examination, N,N'-hydroxydiacetylbis-(3-methylamino-2,4,6-triiodobenzoic acid)-$I^{131}$ and N,N'-adipoylbis(3-amino-2,4,6-triiodobenzoic acid)-$I^{131}$ for liver and gall bladder examination. The use of radioactively labeled compounds in conjunction with various biochemical processes is also known. Tetrachlorotetraiodofluorescein-$I^{131}$, bromthalein-$I^{131}$, and gold colloid $Au^{198}$ have been employed for the liver function test.

The administration of tritium labeled steroids in humans is also known. Chem. Abstracts, 76, 335g (1972).

For a discussion of the use of radioactive tracers in Medicine, see Winchell, H. S., Hospital Practice, October, 1971, pp. 49–60.

It has now been found that radioactively labeled orgotein is useful in scintigraphy, especially for visualization of the kidneys, since the orgotein is rapidly concentrated therein after parenteral administration.

SUMMARY OF THE INVENTION

In a composition aspect, this invention relates to orgotein partially chelated with $^{99m}Tc$. In another composition aspect, this invention relates to orgotein iodinated with a radioactive isotope of iodine, preferably $^{131}I$.

In another composition aspect, this invention relates to pharmaceutical compositions adapted for parenteral administration comprising, in admixture with a pharmaceutically acceptable carrier, a radioactively labeled orgotein of this invention.

In process aspects, this invention relates to processes for the production of the novel compositions of this invention and to methods for their use, particularly in scintigraphy.

DETAILED DISCUSSION

The compact native conformation of the orgotein protein as it conventionally occurs in animals is maintained by about 2 gram atoms per mole (GAPM) each of chelated copper and zinc as the protein exists in its natural state. These chelated metals can be partially and even fully replaced by transchelation by other divalent metals. Bovine and other orgotein congeners which contain tyrosine residues can be labeled with radioactive iodine by iodination of the benzene rings of the tyrosines. It is, therefore, possible to label orgotein with a radioactive metal by chelation or orgotein congeners containing tyrosine residues with a radioactive iodine isotope by iodination.

$^{99M}$Tc is a man-made isotope with a 5 hour half life and internal transition gamma emission only. It decays to $^{99}$Tc with a half life of 200,000 years. Thus, several millicuries of the metastable $^{99M}$Tc will decay in a few days to yield a small fraction of a microcurie of $^{99}$Tc. It is, therefore, an ideal isotope for nuclear medicine. It is the preferred radioactive metal for chelating with orgotein.

Cationic Tc is strongly chelated by orgotein. In the procedures used to label orgotein, pertechnetate ions are reduced by metallic tin to bivalent technetium, which can be chelated by orgotein. The reaction is performed at acid pH to prevent the formation of colloids of tin which can also bind cationic technetium. Once the technetium has been chelated by orgotein, the reaction mixture can be neutralized without significant labelling of the tin colloid.

A conventional method of labeling proteins with a radioactive iodine isotope involves contacting the protein in the cold with a carrier-free radioactive isotope, e.g., $^{131}$I or $^{125}$I, and chloramine-T at a slightly alkaline pH, e.g., about 7.5.

A mild procedure for labeling proteins with $^{125}$I to high specific radioactivities with $^{125}$I-N-succinimidyl 3-(4-hydroxyphenyl)propionate has been described. Bolton and Hunder, Biochem. J. 133, 529 (1973). See also Lou Dilts, Radioassay Symposium, Hartford, Connecticut, May 1974. For procedures for radioiodination of peptides and proteins with bovine lactoperoxidase see Witte, A., et al., Proc. Nat. Acad. Sci., 70, 36 (1973); Miyachi, Y., et al. Endocrinology, 92, 1725 (1973); David, G., et al. Biochem., 13, 1014 (1974); McIlhinney, J., et al., Endocrinology, 94, 1259 (1974); Taurog, A., et al., Ibid., 1286.

The radioactive orgotein is preferably labeled with an amount of $^{99M}$Tc, which imparts a level of radioactivity of about 0.1 to 100, preferably 5 to 10 mCi per mg of orgotein, which corresponds to about $6 \times 10^{-6}$ to $5 \times 10^{-3}$, preferably $10^{-4}$ gram atoms of the radioactive isotope per mole of orgotein (GAPM).

$^{65}$Zn exchange into the orgotein protein (cytocuprein) to a slight extent was observed by Funakoshi, S., et al., J. Biol. Chem., 243, 6474 (1968) and discussed by Carrico, R. J., et al., J. Biol. Chem., 245, 723 (1970). It has also been reported that $^{64}$Cu$^{++}$ added to human blood exchanges into the orgotein protein (erythrocuprein). Schields, G. S., et al., J. Clin. Invest., 40, 2007 (1961).

Similarly, orgotein labeled with $^{125}$I or $^{131}$I preferably has a level of radioactivity of 0.1 to 20, preferably 10 mCi per mg. of orgotein, which corresponds to about $10^{-4}$ to $10^{-1}$, preferably $2 \times 10^{-2}$ ($I^{131}$) or $15 \times 10^{-2}$ ($I^{125}$) GAPM of the radioactive isotope. $^{131}$I-labeled orgotein has a half-life of 8 days, compared to 5 hours for $^{99M}$Tc-labeled orgotein. Less than 1% of the injected dose of radioactive iodine goes to the thyroid when the $^{125}$I or $^{131}$I labeled orgotein is injected, compared to 30 to 40% when radioactive iodine itself is injected.

Contemplated equivalents of the $^{99M}$Tc-labeled orgoteins of this invention are the corresponding $^{64}$Cu, $^{65}$Zn and $^{60}$Co-labeled orgoteins, produced by exchanging a portion of the chelated Cu$^{++}$ and/or Zn$^{++}$ of native orgotein in a manner analogous to that disclosed herein for the production of $^{99}$Tc-labeled orgotein.

The pharmaceutical compositions of this invention comprise a radioactive labeled orgotein of this invention in admixture with a pharmaceutically acceptable carrier. The form and character which this carrier takes is, of course, dictated by the mode of administration.

The pharmaceutical composition preferably is in the form of a sterile injectable preparation, for example, as a sterile injectable aqueous solution. The solution can be formulated according to the known art using those carriers mentioned above. The sterile injectable preparation can also be a sterile injectable solution or suspension in a non-toxic parenterally acceptable diluent or solvent, e.g., 1,3-butanediol.

The compositions of this invention combine an effective unit dosage amount of an orgotein of this invention, i.e., the labeled orgotein is present at a concentration effective to achieve the desired visualization in scintigraphy when a unit dose of the composition is administered by the route applicable for the particular carrier. For example, liquid injectable compositions usually contain about 0.5 to 20 mg of orgotein per 0.25 to 10 cc, preferably about 0.5 to 5 cc. As will be apparent, the minimum dose required to achieve visualization will depend upon the level of radioactivity of the specific sample of orgotein administered. Since the proportion of the administered orgotein which will collect in the kidneys and its level of radioactivity can be determined beforehand, the amount thereof which will be required to achieve satisfactory visualization can readily be calculated.

The labeled orgotein is usually administered intravenously or intramuscularly, usually in a single dose of about 0.5 to 20 mg., preferably about 0.5 to 8 mg. for humans. It will be apparent that in addition to visualization in scintigraphy, the labeled orgotein is also effective in the same manner as unlabeled orgotein, e.g., as disclosed in U.S. Pat. No. 3,758,682.

The labeled orgotein of this invention is particularly useful for the visualization of kidneys in scintigraphy, where the orgotein is rapidly concentrated after intravenous administration within a few minutes. The orgotein has the advantage of providing a non-toxic carrier for the radioactive element and remaining in the kidneys long enough to provide an advantageously long latitude of several hours from the time the labeled orgotein is administered and when scintigraphic examination must be completed.

Without further elaboration, it is believed that one skilled in the art can, using the preceding description, utilize the present invention to its fullest extent. The following preferred specific embodiments are, therefore, to be construed as merely illustrative and not limitative of the remainder of the disclosure in any way whatsoever.

EXAMPLE 1

$^{99M}$Tc-labeled orgotein

To a dry sample of orgotein (1-10 mg.), add 2 shiny tin shot pellets, 1.0 ml. 0.2N HCl and 0.5 ml. pertechnetate. Incubate at room temperature for 10 minutes. The resulting solution can be used as such or neutralized prior to use with 0.2N $Na_2CO_3$.

EXAMPLE 2

$I^{125}$-Iodinated Orgotein

Iodination of orgotein using carrier-free $^{125}$I-labeled iodide was carried out with chloramine-T. Iodination method (NEN): A mixture of 10 mg. orgotein, 10 mCi carrier-free $I^{125}$, 50 mcg. chloramine-T was maintained in 2.5 ml. pH 7.5 0.05M phosphate buffer for 30 minutes at 9° C. Then 75 mcg. sodium metabisulfite was added to stop reaction. 83% of the $I^{125}$ was incorporated into the orgotein molecule as shown by Sephadex G-25 chromatography. The labeled orgotein has a specific activity of 0.5 mCi/mg. and a radiometric purity of 99% with less than 2% contamination by inorganic iodide after purification on a Sephadex-25 column. The solution (approximately 10 mg. orgotein in 4.8 ml.) is frozen. The electrophoretic behavior and superoxide dismutase activity of the orgotein is not altered by the iodination procedure.

Following the procedure of Example 2 but substituting $I^{131}$ for $I^{125}$, $I^{131}$-labeled orgotein having about the same radioactivity as the product of Example 2 is produced.

EXAMPLE A

Kidney Visualization With Technetium-Orgotein $^{99M}$Tc-labeled orgotein obtained by adding to 1-10 mg. dry samples of orgotein, 2 tin shot pellets (shiny), 1.0 ml. 0.02N HCl and .5 ml. pertechnetate (5-20 mCi) followed by 10 minutes incubation at room temperature and thereafter, when neutralization prior to injection was desird, followed by 1 ml. of 0.02N $Na_3CO_3$, was employed in the experiments.

In dogs, intravenous injection of 0.4-1 cc. of solution containing 2 to 5 mCi of $^{99M}$Tc-labeled orgotein was used for kidney imaging.

Radiation Detection:

$^{99M}$Tc distributions were imaged on Polaroid film exposed to the output oscilloscopes of pinhole cameras manufactured by Picker Nuclear, Inc. and by Nuclear Chicago Corporation. Quantitative data was obtained by using the digital integration mode of the same instruments. Counting geometry was constant within each experiment.

Organ Counting:

Rats were anaesthetized with pentabarbital either prior to injection with labelled orgotein or just before sacrifice. Organs were dissected and positioned under the pinhole camera. Centering was checked with the aid of the oscilloscope display. Background was subtracted when it represented more than 1% of the count rate.

Blood and Urine:

Blood samples were obtained by severing the aorta of anaesthetized rats during dissection. Urine samples were removed from the bladders of dissected rats with a 27 ga. needle and 3 ml. syringe.

Injection Site Counting:

Radioactivity at subcutaneous injection sites was measured by integrating over the portion of the field occupied by the injection site, using a Picker camera. The integration was repeated at the times indicated.

Photographic Imaging:

Rats were positioned for imaging of $^{99M}$Tc distributions within two minutes after tail-vein injection of labelled orgotein. The kidneys already appeared labelled nearly as well as the liver and heart (representing blood pools). Subsequently, the radioactivity clears from the blood pool and becomes more concentrated in the kidneys, so that by 15 minutes the kidneys dominate the pictures. A trace of activity appears in the urine by 15 minutes which does not increase much, even to four hours. The radioactivity in the kidneys persists. Neutralization of the solution to be injected does not influence the patterns observed. After subcutaneous, intraperitoneal or intramuscular administration of $^{99M}$Tc-orgotein to anaesthetized rats nearly all of the radioactivity remains at the injection site (with the i.p. route it fills the peritoneal cavity and remains there). In unanaesthetized rats the label slowly leaves the injection site and appears in the kidneys. Roughly equal image intensities for injection site and kidneys are attained after two hours. Skinning at three hours revealed a diffuse distribution of radioactivity over the entire carcass and pelt, with hot spots at the injection sites. A similar rapid clearance of $^{99M}$Tc-orgotein by the kidneys was observed with two dogs after intravenous administration.

Close-up pictures of the kidneys of the intact dogs revealed that the label in the kidneys was localized principally in the cortex. Adrenal labelling was not apparent.

Counts of the organs of dissected rats verified the role of the kidneys in serum clearance of $^{99M}$Tc-orgotein. Blood samples representing about one-third to one-fourth of the calculated blood volume of the animals contained no more than 2% of the total radioactivity by 30 minutes after i.v. injection. By this time, one-third to two-thirds of the total radioactivity was in the kidneys. A small dose dependence was observed for kidney accumulation, with a higher fraction of the injected dose appearing in the kidneys at the higher orgotein doses.

Between 30 minutes and 24 hours after injection, orgotein continued to be cleared from the liver, lung, spleen and stomach, resulting in an increase in the fraction of the radioactivity seen in the kidney and the carcass. Urine contained a few hundredths of the total radioactivity at all times studied.

Following subcutaneous injection of $^{99M}$Tc-orgotein in anaesthetized rats no significant mobilization of the label from the injection site occurs. However, when the same procedure is applied to unanaesthetized rats, mobilization does occur and one-third of the label appears in the kidneys at two hours. Blood radioactivity is not detectable, resulting in very low activities in the liver, lungs, spleen and stomach. The diffuse labelling of the carcass and skin then accounts for about half of the total activity.

After i.p. injection in anaesthetized rats, $^{99M}$Tc-orgotein behaved in a fashion intermediate between that seen in s.c. and i.v. dosed animals under anaesthesia. Some kidney accumulation was measurable at 30 minutes, at which time blood and liver contained several hundredths of the label.

EXAMPLE B

Administration of $^{125}$I-Orgotein

Each dog was acclimatized to the assigned metabolism cage for 1 week before the experiment. Dog 1 was injected intravenously in the forelimb with 0.4 ml of $^{125}$I-orgotein. Blood samples were taken either from the vein of the forelimb or the jugular, at 15-minute intervals until sacrifice 3 hours after injection. Dog 2 was injected subcutaneously at the back of the neck with 0.8 ml of $^{125}$I-orgotein. Blood samples were taken at 30-minute intervals until sacrifice 6 hours after injection. Dog 3 also was injected subcutaneously with 1.2 ml each of 125I-orgotein. The dogs were not anaesthetized at any time during the experiment. Daily urinary and fecal samples were collected until sacrifice 12 days after injection.

After sacrifice, the major internal organs were removed and the total weight of each organ was recorded. Representative samples of each organ (e.g., portions of lung or liver from each lobe or different regions of intestines) were taken for radioactivity determination. Tissue samples were counted after homogenization with three parts (w/v) of water. Tissues that were not completely homogenized because of toughness were counted as homogenates as well as residues to obtain the total count. All samples (0.1 to 1 ml) were counted in duplicates using the Nuclear-Chicago automatic gamma counter, Model 4224.

A set of standards prepared at the beginning of the experiment was counted each time the samples were counted. The loss in radioactivity as a result of the natural decay of $^{125}$I was corrected by relating the daily standard counts back to the initial counts of the standards. The counting data were used to calculate the specific activity (cpm/ml or g) of a tissue and the percentage of administered dose found in each tissue. For the latter calculation, an assumption was made that blood, muscle, and fat correspond to 9.4, 40, and 15% respectively, of the body weight.

After intravenous administration of 0.4 ml of a solution of approximately 0.8 mg of freshly prepared $^{125}$I-labeled orgotein ($6 \times 10^8$ total cpm) to DOG 1 (8.9 kg), the plasma radioactivity declined with an initial biological half-life of less than 15 minutes ($2.7 \times 10^5$ cpm/ml) of blood). The radioactivity level in the blood changed little between 45 minutes and 3 hours post-injection. After 3 hours, the specific activity (cpm/g) of the radioactivity in the tissue was highest in thyroid ($6.4 \times 10^6$ cpm/g). Kidney ($1.3 \times 10^6$ cpm/g), bladder content ($6.6 \times 10^5$ cpm/g), and stomach ($5.6 \times 10^5$ cpm/g) showed higher specific activity than did blood. On the basis of low specific activity of the bile and small intestine, biliary excretion is not considered to be a major elimination route for $^{125}$I-orgotein.

After subcutaneous administration of 0.8 ml of a solution of approximately 1.6 mg of the $^{125}$I-orgotein ($1.2 \times 10^9$ total cpm to Dog 2 (8.8 kg), a sharp peak of $^{125}$I in the blood was not observed. The radioactivity rose gradually for 6 hours. The tissue distribution of radioactivity after subcutaneous administration was similar to that seen at the end of the intravenous experiment. Thyroid, kidney, bladder content, and stomach had higher specific activity than did blood.

A dog weighing 9.3 kg (Dog 3) was injected subcutaneously with approximately 2.4 mg each of $^{125}$I-orgotein, and excretion of radioactivity was followed for 12 days. The dog almost quantitatively excreted the radioactive dose in urine by the fourth day. Fecal excretion accounted for only 1% of the dose. After 12 days, thyroid still retained 2.3% of the administered dose. The specific activity was higher in thyroid, kidney, liver, subcutaneous fat and lung than in blood.

Radioactivity in the whole blood of Dog 1 after intravenous injection of orgotein declined initially with a halflife of less than 15 minutes. After a slow equilibration period of 45 minutes, the blood radioactivity remained essentially unchanged until sacrifice, 3 hours after injection. Thyroid showed the highest specific activity. This finding cannot be taken as evidence of extensive deiodination of $^{125}$I-orgotein, since the total radioactivity present in the gland is less than the 1 to 2% contamination of orgotein with inorganic $^{125}$I. Concentrations of radioactivity higher than that in the whole blood were observed in kidney bladder content, and stomach. These amounts may represent inorganic $^{125}$I or orgotein-bound $^{125}$I on their way to being excreted. $^{125}$I is almost exclusively eliminated via the kidney. The reason for the high concentration of radioactivity in the stomach cells is not clear. It may represent an attempt by the stomach cells to secrete either the free or bound form of $^{125}$I. The low specific activity of the bile eliminates biliary excretion as playing any significant role in the elimination of $^{125}$I-orgotein.

After subcutaneous administration of $^{125}$I-orgotein in Dog 2, the blood radioactivity level rose gradually over a 6-hour period without any clear peak. A comparison of the blood levels between Dog 1 and Dog 2 indicates that approximately half of the subcutaneous dose eventually found its way into the blood after 3 hours, and that amount kept increasing for an additional 3 hours. The tissue distribution of radioactivity after subcutaneous injection was similar to that seen in the intravenous experiment. Thyroid, kidney, bladder content and stomach had higher specific activity than the blood of Dog 2. Assay of tissues at the site of injection indicated that less than 1% of the injected dose remained at the site. The (39.6%) overall accountability of radioactivity in Dog 2 is low compared with the 59.1% obtained in the intravenous experiment in Dog 1.

After subcutaneous injection of approximately 2.4 mg of $^{125}$I-orgotein to Dog 3, the excretion of radioactivity was monitored daily for 12 days. Dog 3 excreted the radioactivity almost quantitatively by Day 4, with very little excretion in the feces. In Dog 3, thyroid showed by far the highest specific activity among all tissues and still retained over 1% of the administered dose.

Kidney, liver and lung showed specific activity equal to or larger than that of blood. The adrenal, spleen and the digestive tracts showed intermediate levels of specific activity.

EXAMPLE C

Following the procedure of Example B, kidney visualization is achieved with $^{131}$I-labeled orgotein having the same level of radioactivity per gram as the $^{125}$I-labeled orgotein.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. Orgotein radioactively labeled with chelated $^{99m}$Tc.

2. Radioactively labeled orgotein according to claim 1, labeled with $10^{-2}$ to $10^2$ mCi/mg of chelated $^{99m}$Tc.

3. A radioactively labeled orgotein according to claim 1, wherein the orgotein is bovine orgotein.

4. Radioactively labeled orgotein according to claim 3, labeled with $10^{-2}$ to $10^2$ mCi/mg of chelated $^{99M}$Tc.

5. An iodinated tyrosine-containing orgotein congener iodinated with a radioactive isotope of iodine.

6. An iodinated orgotein according to claim 5, iodinated with $^{125}$I.

7. An iodinated orgotein according to claim 6, having a radioactivity of 0.1 to 20 mCi/mg of $^{125}$I.

8. An iodinated orgotein acccording to claim 7, wherein the orgotein congener is bovine orgotein.

9. A method of visualizing the kidneys by scintigraphy which comprises administering intraveously a kidney visualizing amount of a compound of claim 1.

10. A method of visualizing the kidneys by scintigraphy which comprises administering intravenously a kidney visualizing amount of a compound of claim 5.

* * * * *